United States Patent [19]
Torii et al.

[11] 4,186,141
[45] Jan. 29, 1980

[54] PROCESS FOR PREPARING 2-PENTYNYL ETHER

[75] Inventors: Sigeru Torii; Yuichi Kobayashi; Hideo Tanaka, all of Okayama, Japan

[73] Assignee: Otsuka Kagaku Yakuhin Kabushiki Kaisha, Osaka, Japan

[21] Appl. No.: 932,311

[22] Filed: Aug. 9, 1978

[30] Foreign Application Priority Data

Dec. 28, 1977 [JP] Japan .................................. 52 6799

[51] Int. Cl.$^2$ ..................... C07D 309/06; C07C 43/14
[52] U.S. Cl. ............................. 260/345.9 R; 568/673
[58] Field of Search .................. 260/345.9 R, 615 R; 568/673

[56] References Cited

U.S. PATENT DOCUMENTS

| 3,806,540 | 4/1974 | Martel et al. ................ 260/345.9 R |
| 3,975,409 | 8/1976 | Eiter .............................. 260/345.9 R |
| 3,996,270 | 12/1976 | Friedman et al. ............ 260/345.9 R |

OTHER PUBLICATIONS

Rachlin et al., J. Org. Chem., 26, 2688 (1961).

*Primary Examiner*—Nicky Chan
*Attorney, Agent, or Firm*—Armstrong, Nikaido, Marmelstein & Kubovcik

[57] ABSTRACT

A process for preparing 2-pentynyl ether represented by the formula

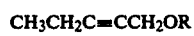

$$CH_3CH_2C\equiv CCH_2OR$$

wherein R is tetrahydropyranyl and methoxyethyl characterized by reacting propargyl ether represented by the formula $HC\equiv CCH_2OR$ wherein R is as defined above with an ethyl halide in a nonprotonic polar solvent in the presence of a metal hydride.

4 Claims, No Drawings

PROCESS FOR PREPARING 2-PENTYNYL ETHER

This invention relates to a process for preparing 2-pentynyl ether.

2-Pentynyl ether is usually prepared by reacting propargyl ether with ethyl halide in the presence of a base such as n-BuLi, NaNH$_2$, RMgX or the like but the process is not suited to commercial operation because the base must be handled with special care, the reaction must be conducted in liquid ammonia and the reagent is expensive, giving low yields.

An object of this invention is to provide a process for preparing 2-pentynyl ether in much higher yields and with greater ease and safety than the conventional process.

Another object of this invention is to provide a process for preparing 2-pentynyl ether with a reduced likelihood of giving pollutants, high amenability to commercial operation and economical advantages.

The present invention provides a process for preparing 2-pentynyl ether represented by the formula CH$_3$CH$_2$C≡CCH$_2$OR wherein R is tetrahydropyranyl and methoxyethyl characterized by reacting propargyl ether represented by the formula HC≡CCH$_2$OR wherein R is as defined above with an ethyl halide in a nonprotonic polar solvent in the presence of a metal hydride.

The compound of this invention is useful as a material for the synthesis of jasmonoid compounds well known for example as components of perfumes. In the synthesis of jasmonoid compounds which are ketone derivatives of five-membered ring having a cis-2-pentenyl group on the side chain, how to introduce the cis-2-pentenyl group is an important problem. Generally this is done with use of a 2-pentynyl halide. The present compound is useful as an intermediate for the synthesis of such 2-pentynyl halide. In view of the attention presently focused on jasmonoid and prostanoid compounds, this invention provides an economically advantageous industrial process.

Propargyl tetrahydropyranyl ether and propargyl methoxyethyl ether, starting materials of this invention, are known compounds which can be easily produced, for example, from propargyl alcohol and dihydropyran, or propargyl alcohol and methyl vinyl ether. It is possible to use another alkyl vinyl ether in place of methyl vinyl ether serving as a protecting group for the hydroxyl group. The reaction between propargyl alcohol and dihydropyran, or propargyl alcohol and methyl vinyl ether is conducted in the presence of an acid catalyst such as p-toluenesulfonic acid at about −10° to about +50° C., preferably at a low temperature immediately after the addition of the catalyst and at room temperature thereafter.

The process of this invention is characterized in that the propargyl tetrahydropyranyl ether or propargyl methoxyethyl ether thus obtained is reacted with an ethyl halide in a nonprotonic polar solvent in the presence of a metal hydride. Examples of useful ethyl halides are ethyl chloride, ethyl bromide, ethyl iodide, etc. The ethyl halide is used in an amount of about 1.1 to about 5 moles, preferably about 1.3 to about 2 moles, per mole of propargyl tetrahydropyranyl ether or propargyl methoxyethyl ether, although the amount is not particularly limited. Examples of useful nonprotonic polar solvents are tetrahydrofuran (THF), diethyl ether, dimethoxyethane, dimethylformamide (DMF), etc. Although various metal hydrides are usable, it is especially preferable to use sodium hydride, lithium hydride and calcium hydride. Preferably the metal hydride is used in an amount of about 1.1 to about 3 moles per mole of propargyl tetrahydropyranyl ether or propargyl methoxyethyl ether. The reaction is conducted either at atmospheric pressure or at increased pressure. The reaction temperature, although not particularly limited, is preferably 0° C. to the reflux temperature of the solvent used. When tetrahydrofuran, diethyl ether, dimethoxyethane or like ether is used as solvent, it is particularly preferable to effect the reaction at about 25° C. to the reflux temperature. With use of dimethylformamide, the reaction proceeds favorably at about 15° C. to the reflux temperature.

The desired compound of this invention resulting from the process described above can be easily purified by a known method such as extraction, distillation or chromatography.

Examples of this invention and Comparison Examples are given below.

EXAMPLE 1

Propargyl alcohol (13.20 g) and dihydropyran (19.81 g) are placed into a 50-ml container, and 0.2 g of anhydrous p-toluenesulfonic acid is added. The mixture is cooled in an ice bath, then stirred at room temperature for 30 minutes and neutralized with anhydrous sodium carbonate. The resulting solids are separated off. Distillation of the remaining liquid in a vacuum gives 31.3 g of propargyl tetrahydropyranyl ether (yield: 95%), b.p. 75° to 80° C./37 mm Hg.

IR (cm$^{-1}$): 3277 (C≡C), 2940, 2865, 2055 (C≡C); NMR (CCl$_4$):

δ 4.67 (s, 1H, O—CH—O); 4.11 (W, J=2, 5 Hz, 2H, C≡CCH$_2$—O); 3.13–3.94 (m, 2 H, CH$_2$—O); 2.32 (t, J=2, 5Hz, 1H, CH≡C).

THF (2 ml) is added to 68 mg of sodium hydride (content: 47%), and 293 mg of ethyl iodide and 100 mg of the propargyl tetrahydropyranyl ether obtained as above is added to the mixture. The resulting mixture is refluxed for 12 hours and then cooled to room temperature. Several droplets of water are added to the mixture. After the evolution of hydrogen gas has ceased, one ml of 10% aqueous solution of ammonium chloride is added to the reaction mixture, and the mixture is then extracted with ether. The solvent is distilled off, and the residue is further distilled in a vacuum, giving 2-pentynyl tetrahydropyranyl ether, the desired product. The yield resulting from purification by column chromatography (SiO$_2$) is 94%, b.p. 110°–113° C./17 mm Hg. (In the following examples, the product will be purified similarly.)

IR (cm$^{-1}$): 2948, 2872, 2224 (C≡C), 1120, 1024; NMR (CCl$_4$):

δ4.73 (s, 1H, O—CH—O); 4.10 (t, J=2, 1 Hz, 2H, O—CH$_2$—C≡C); 3.20–4.00 (m, 2H, CH$_2$—O); 1.94–2.46 (m, 2H, CH$_2$—C≡C); 1.17 (t, J=12 Hz, 3H, CH$_3$—).

EXAMPLE 2

A 2 ml quantity of DMF is added to 65 mg of sodium hydride (content: 47%), and 280 mg of ethyl iodide and 100 mg of propargyl tetrahydropyranyl ether are further added. The mixture is stirred at 18° to 20° C. for 24 hours, and several droplets of water are added to the mixture. After the evolution of hydrogen gas has ceased, one ml of 10% aqueous solution of ammonium chloride is added to the reaction mixture. The resulting mixture is extracted with ether. The solvent is distilled off, and the residue is distilled in a vacuum to obtain the desired product in a yield of 77%, b.p. 119°–120° C./20 mm Hg.

EXAMPLE 3

A 2 ml quantity of THF is added to 45 mg of sodium hydride (content: 47%), and 130 mg of ethyl bromide and 100 mg of propargyl tetrahydropyranyl ether are further added. The mixture is heated at 83° to 86° C. for 8 hours in a closed tube and thereafter allowed to cool. The tube is then opened to add several droplets of water. After the evolution of hydrogen gas has ceased, one ml of 10% aqueous solution of ammonium chloride is added to the reaction mixture. The mixture is extracted with ether. The solvent is distilled off, and the residue is further distilled in a vacuum to obtain the desired product in a yield of 98%, b.p. 105°–109° C./16 mm Hg.

EXAMPLE 4

Propargyl alcohol (13.20 g) and methyl vinyl ether (14.5 g) are placed into a 50-ml container, and 0.5 g of anhydrous p-toluenesulfonic acid is added. The mixture is cooled in an ice bath, then stirred at room temperature for 30 minutes and neutralized with anhydrous sodium carbonate. The resulting solids are separated off. Distillation of the remaining liquid in a vacuum gives 25.8 g of propargyl methoxyethyl ether (yield: 96%).

THF (2 ml) is added to 65 mg of sodium hydride (content: 47%), and 295 mg of ethyl iodide and 75 mg of the propargyl methoxyethyl ether obtained as above is added to the mixture. The resulting mixture is treated in the same manner as in Example 1. The pentynyl methoxyethyl ether, the desired product, is obtained in 92% yield.

Elementary analysis:

|         | C      | H     | O      |
|---------|--------|-------|--------|
| Calcd.  | 67.61% | 9.86% | 22.53% |
| Found   | 67.59% | 9.85% | 22.56% |

IR (cm$^{-1}$): 2947, 2222 (C≡C); NMR (CCl$_4$): δ4.10 (t, J=2, 1 Hz, 2H, O—CH$_2$—C≡C); 3.20–4.00 (m, 2H, CH$_2$—O); 1.93–2.45 (m, 2H, CH$_2$—C≡C).

COMPARISON EXAMPLE 1

A 50-ml dry flask is cooled to −70° C. with dry ice-ethanol, and ammonia gas is introduced into the flask and liquefied. About 30 ml of liquid ammonia is withdrawn to which about 0.8 g of metal sodium is added. The mixture is refluxed for one hour, and 0.92 g of metal sodium is further added to the mixture. After confirming that sodium amide has been formed, 5 g of propargyl tetrahydropyranyl ether is added dropwise to the mixture. The resulting mixture is refluxed for about one hour, 4.36 g of ethyl bromide is slowly added dropwise to the mixture and the mixture is refluxed for one hour. The liquid ammonia is thereafter evaporated off. With addition of ether and then with addition of water to the residue, the excess of sodium amide is decomposed. The resulting mixture is extracted with ether, the ethereal layer is washed with a saturated aqueous solution of sodium chloride, and the ether is distilled off. Distillation of the residue in a vacuum affords the desired product in a yield of 63%.

COMPARISON EXAMPLE 2

The procedure of Example 1 is repeated except that sodium methylate (CH$_3$ONa) is used in place of sodium hydride. As a result, the starting material is merely recovered.

COMPARISON EXAMPLE 3

The procedure of Example 1 is repeated except that sodium hydroxide is used in place of sodium hydride. As a result, the starting material is merely recovered.

COMPARISON EXAMPLE 4

The procedure of Example 2 is repeated except that the reaction is carried out at 59° to 60° C. for 7 hours with use of benzene, nonpolar solvent, in place of DMF. Consequently, the starting material is merely recovered.

What is claimed is:

1. A process for preparing 2-pentynyl ether represented by the formula

CH$_3$CH$_2$C≡CCH$_2$OR wherein R is tetrahydropyranyl and methoxyethyl characterized by reacting propargyl ether represented by the formula HC≡CCH$_2$OR wherein R is as defined above with an ethyl halide in a nonprotonic polar solvent in the presence of a metal hydride selected from the group consisting of sodium hydride, lithium hydride and calcium hydride.

2. A process as defined in claim 1 wherein the nonprotonic polar solvent is tetrahydrofuran, diethyl ether, dimethoxyethane or dimethylformamide.

3. A process as defined in claim 1 wherein the metal hydride is used in an amount of about 1.1 to about 3 moles per mole of propargyl tetrahydropyranyl ether or propargyl methoxyethyl ether.

4. A process as defined in claim 1 wherein the ethyl halide is used in an amount of about 1.1 to about 5 moles per mole of propargyl tetrahydropyranyl ether or propargyl methoxyethyl ether.

* * * * *